United States Patent [19]

Hinshaw et al.

[11] 4,126,616

[45] Nov. 21, 1978

[54] N-PROPYLNORAPOMORPHINE DIESTERS

[75] Inventors: William Banks Hinshaw, Sand Lake; Jack Pearl, Bethlehem, both of N.Y.

[73] Assignee: William B. Hinshaw, New York, N.Y.

[21] Appl. No.: 749,721

[22] Filed: Dec. 13, 1976

Related U.S. Application Data

[63] Continuation-in-part of Ser. No. 630,722, Nov. 10, 1975, abandoned.

[51] Int. Cl.$^2$ .................. C07D 215/20; C07D 215/22
[52] U.S. Cl. ...................................... 546/75; 424/258
[58] Field of Search ............... 260/287 P, 285, 286 R

[56] References Cited

U.S. PATENT DOCUMENTS

| | | | |
|---|---|---|---|
| 3,717,639 | 2/1973 | Neumeyer | 260/285 |
| 3,717,643 | 2/1973 | Archer | 260/285 |

FOREIGN PATENT DOCUMENTS 2,154,162  5/1973  Fed. Rep. of Germany ....... 260/287 P

OTHER PUBLICATIONS

Lecomte et al., Chem. Abstracts, vol. 58, 6104d (1962).
Ibid Janssen et al., vol. 55, 8659f (1960).
Cannon et al. "J. Pharm Sci."52(11), 1112–1113 (1963).
Dictionary of Organic Compounds, Oxford Press (1965).

*Primary Examiner*—Donald G. Daus
*Assistant Examiner*—David E. Wheeler
*Attorney, Agent, or Firm*—William G. Webb; B. Woodrow Wyatt

[57]  ABSTRACT

N-Propylnorapomorphine dialkanoate, dibenzoate and dicyclopropanecarboxylate esters and acid-addition salts thereof, having anti-parkinson activity, are prepared by reaction of N-propylnorapomorphine with a respective alkanoyl, benzoyl or cyclopropanecarbonyl halide or corresponding acid anhydride in the presence of an acid acceptor.

19 Claims, No Drawings

N-PROPYLNORAPOMORPHINE DIESTERS

RELATED APPLICATIONS

This is a continuation-in-part of our prior, copending application Ser. No. 630,722, filed Nov. 10, 1975 now abandoned.

BACKGROUND OF THE INVENTION (a) Field of the Invention

This invention relates to N-propylnorapormorphine dialkanoate, dibenzoate and dicyclopropanecarboxylate esters useful as anti-parkinson agents.

(b) Description of the Prior Art

Archer, U.S. Pat. No. 3,717,643, patented Feb. 20, 1973, discloses N-propylnorapomorphine useful as an emetic, hypotensive and CNS stimulant. German application No. 2,154,162, published May 3, 1973, discloses a variety of O,O-diacylapomorphines, useful as anti-parkinson agents.

SUMMARY

In a composition of matter aspect, the invention relates to N-propylnorapomorphine dialkanoate, dibenzoate and dicyclopropanecarboxylate esters and acid addition salts thereof useful as anti-parkinson agents.

In a process aspect, the invention relates to a process for preparing N-propylnorapomorphine dialkanoate, dibenzoate and dicyclopropanecarboxylate esters comprising reacting N-propylnorapomorphine with at least two molar equivalents of a respective alkanoyl, benzoyl or cyclopropanecarbonyl halide or corresponding acid anhydride in the presence of an acid acceptor.

DETAILED DESCRIPTION INCLUSIVE OF THE PREFERRED EMBODIMENTS

More specifically, the invention relates to N-propylnorapomorphine dialkanoate, dibenzoate and dicyclopropanecarboxylate esters, which are useful as anti-parkinson agents, having the formula:

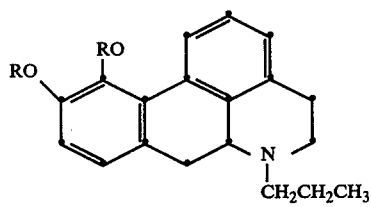

where R is alkanoyl, benzoyl or cyclopropanecarbonyl.

As used herein the term alkanoyl means a saturated, aliphatic group derived from a monocarboxylic alkanoic acid, which may be straight or branched, and containing from two to twenty carbon atoms, as illustrated by, but not limited to acetyl, propionyl, butyryl, isobutyryl, pentanoyl (i.e. valeroyl), 2,2-dimethylpropanoyl (i.e., pivaloyl), decanoyl, hexadecanoyl, eicosanoyl and the like.

The benzoyl group can be unsubstituted or substituted by from one to three halogen atoms (including fluorine, chlorine or bromine) or by from one to three methyl or methoxy groups.

The N-propylnorapomorphine esters of formula I are prepared by reaction of the corresponding N-propylnorapomorphine with at least two molar equivalents of an appropriate alkanoyl, benzoyl or cyclopropanecarbonyl halide or the corresponding acid anhydride in the presence of an acid acceptor, for example pyridine, triethylamine, diethylaniline, and the like. The reaction is preferably carried out at a temperature in the range from about −10° to about 50° C. and may be carried out either with or without a solvent. Suitable solvents when used are pyridine, benzene, toluene, ethylene dichloride, and the like. It is preferred to carry out the reaction in excess pyridine as both solvent and acid acceptor.

The novel compounds of the instant invention are the compounds of formula I and the acid-addition salts thereof. The compounds of formula I in free base form are converted to the acid-addition salt form by interaction of the bases with an acid. In like manner, the free bases can be regenerated from the acid-addition salt form in conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formula I not only represents the structural configuration of the bases of formula I but is also representative of the structural entity which is common to all forms of the compounds of formula I, whether in the form of the free bases or in the form of the acid-addition salts of the bases. It has been found that by virtue of this common structural entity, the bases and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically acceptable acids, that is acids whose anions are innocuous to the animal organism in effective doses of the salts so that beneficial properties inherent in the common structural entity represented by the free bases are not vitiated by side effects ascribable to the anions.

In utilizing this pharmacological activity of the salts of the invention, it is preferred, of course, to use pharmaceutically acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically acceptable bases by decomposition of the salt with aqueous base as explained above, or alternatively they can be converted to any desired pharmaceutically acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically acceptable free bases by reaction of the salts with aqueous base, or alternatively they can be converted to a pharmaceutically acceptable acid-addition salt by, for example, ion-exchange procedures.

It will be appreciated from the foregoing that all of the acid-addition salts of the new bases are useful and valuable compounds, regardless of considerations of solubility, toxicity, physical form and the like, and are accordingly within the purview of the instant invention.

The novel feature of the compounds of the invention, then, resides in the concept of the base and cationic forms of the new N-propylnorapomorphine diesters and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases. In fact, in aqueous solutions, the base form or water-soluble acid-addition salt form of the compounds of the invention both possess a common protonated cation or ammonium ion.

Thus appropriate acid-addition salts are those derived from such diverse acids as formic acid, acetic acid, isobutyric acid, γ-aminobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzene sulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and acid in an organic solvent and isolating the salt directly or by concentration of the solution.

In a standard pharmacological test procedure, the compounds of formula I have been found to possess anti-parkinson activity and are thus useful as anti-parkinson agents. An index of anti-parkinson activity was determined using the caudate lesioned mouse test described by Lotti, Life Sci., 10, 781–789 (1971). The mice having unilateral lesions of the caudate nucleus prepared according to the method of Lotti supra were observed immediately after the surgical procedure for strong postural asymmetries directed to the same side as the lesion. When this asymmetry was not observed, the mice were discarded. Operated mice were allowed at least 14 days to recover prior to drug testing. The lesioned mice were tested with apomorphine using 1.7 mg./kg. of base administered intraperitoneally in a 1% suspension in gum tragacanth. The mice were observed in an open field for postural asymmetries and circling movements ipsilateral to the lesioned side at 10, 15 and 20 minutes following apomorphine injection. Only those mice which twisted or circled toward the lesioned side in all three test periods after the apomorphine injection were retained for further drug testing. The test drugs were all administered in 1% gum tragacanth suspension in a volume of 0.1 ml./10 g. of body weight. Doses were expressed in mg./kg. of free base. If the caudate lesioned mouse reponded by postural asymmetry or by circling movements ipsilateral to the operated side at least once during one of three post-drug observation periods, the mouse was scored as having exhibited a positive response.

The compounds of the invention are preferably administered orally and can be prepared for use by incorporating them in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol or oil solutions or oil-water emulsions in the same manner as conventional medicinal substances are prepared.

The molecular structures of the compounds of the invention were assigned on the basis of study of their infrared, ultraviolet and NMR spectra, and confirmed by the correspondence between calculated and found values for elementary analyses for the elements.

The following examples will illustrate the best mode of carrying out the process of the invention. All melting points are uncorrected.

EXAMPLE 1

A solution of 9.96 g. (0.03 mole) of N-propylnorapomorphine hydrochloride (Archer, U.S. Pat. No. 3,717,643) in 50 ml. of absolute pyridine was chilled in an ice bath, the reaction flask was flushed with nitrogen, and the solution treated dropwise over a period of ten minutes with 11.1 g. (0.12 mole) of propionyl chloride. When addition was complete, the reaction mixture was allowed to warm to ambient temperature, filtered and the solid filter washed once with pyridine. The combined filtrates were added to 600 ml. of diethyl ether, and the resulting precipitate was dissolved in chloroform. The organic solution was extracted once with water containing a little hydrochloric acid, once with saturated sodium bicarbonate, and once with brine, dried over sodium sulfate, filtered and concentrated to dryness to give 13 g. of a thick yellow oil which slowly crystallized. The latter was recrystallized from isopropanol to give two crops of product totalling 7.55 g. which were combined and recrystallized once again from 70 ml. of isopropanol to give 6.3 g. of N-propylnorapomorphine dipropionate, m.p. 112°–113° C.

A small sample of the free base was converted to the hydrochloride salt in methanolic hydrogen chloride and the salt recrystallized from methanol/diethyl ether to give the corresponding hydrochloride, m.p. 209°–211° C.

EXAMPLES 1A–1P

Following a procedure similar to that described in Example 1 above, the following compounds of formula I were also prepared:

1A. N-Propylnorapomorphine dibutanoate, m.p. 88°–89° C. (8.9 g. from hexane), by reaction of 9.96 g. (0.03 mole) of N-propylnorapomorphine hydrochloride with 7.46 g. (0.07 mole) of butyryl chloride in 50 ml. of pyridine;

1B. N-Propylnorapomorphine diisobutyrate, m.p. 119°–120° C. (8.0 g. from isopropanol), by reaction of 9.96 g. (0.03 mole) of N-propylnorapomorphine hydrochloride with 9.6 g. (0.09 mole) of isobutyryl chloride in 50 ml. of pyridine;

1C. N-Propylnorapomorphine dipivaloate, m.p. 144°–146° C. (8.7 g. from isopropanol), by reaction of 9.96 g. (0.03 mole) of N-propylnorapomorphine hydrochloride with 18.0 g. (0.15 mole) of pivaloyl chloride in 50 ml. of pyridine;

1D. N-Propylnorapomorphine dihexadecanoate, m.p. 60.5°–62.5° C. (15.5 g. from acetone), by reaction of 13.28 g. (0.04 mole) of N-propylnorapomorphine hydrochloride with 27.5 g. (0.1 mole) of hexadecanoyl chloride in 75 ml. of pyridine;

1E. N-Propylnorapomorphine dibenzoate hydrochloride, m.p. 170°–175° C. (9.5 g. from methanol/diethyl ether), by reaction of 9.96 g. (0.03 mole) of N-propylnorapomorphine hydrochloride with 16.9 g. (0.12 mole) of benzoyl chloride in 50 ml. of pyridine;

1F. N-Propylnorapomorphine bis-4-chlorobenzoate, m.p. 168°–169° C. (6.0 g. from isopropanol/n-butanol), by reaction of 7.5 g. (0.023 mole) of N-propylnorapomorphine hydrochloride with 15.8 g. (0.09 mole) of 4-chlorobenzoyl chloride in 40 ml. of pyridine;

1G. N-Propylnorapomorphine bis-2-methylbenzoate, m.p. 120°–121° C. (6.5 g. from ethanol), by reaction of 6.64 g. (0.02 mole) of N-porpylnorapomorphine hydrochloride with 9.24 g. (0.06 mole) of 2-methylbenzoyl chloride in 50 ml. of pyridine;

1H. N-Propylnorapomorphine bis-4-methylbenzoate, m.p. 157°–158° C. (3.0 g. from acetone), by reaction of 3.33 g. (0.01 mole) of N-propylnorapomorphine hydrochloride with 9.28 g. (0.06 mole) of 4-methylbenzoyl chloride in 100 ml. of pyridine;

1J. N-Propylnorapomorphine bis-4-methoxybenzoate, m.p. 188°–190° C. (9.0 g. from ethyl acetate), by reaction of 9.96 g. (0.03 mole) of N-propylnorapomorphine hydrochloride with 20.4 g. (0.12 mole) of 4-methoxybenzoyl chloride in 50 ml. of pyridine;

1K. N-Propylnorapomorphine bis-3,5-dimethoxybenzoate hydrochloride, m.p. 223°–225° C. (5.5 g. from ethanol/diethyl ether), by reaction of 6.64 g. (0.02 mole) of N-propylnorapomorphine hydrochloride with 16 g. (0.08 mole) of 3,5-dimethoxybenzoyl chloride in 50 ml. of pyridine;

1L. N-Propylnorapomorphine bis-3,4,5-trimethoxybenzoate hydrochloride, m.p. 230°–231° C. (16.5 g. from ethanol/ether), by reaction of 9.96 g. (0.03 mole) of N-propylnorapomorphine hydrochloride with 16.2 g. (0.07 mole) of 3,4,5-trimethoxybenzoyl chloride in 50 ml. of pyridine; and 1M. N-Propylnorapomorphine bis-cyclopropanecarboxylate, m.p. 119°–120° C. (6.6 g. from ethyl acetate), by reaction of 9.96 g. (0.03 mole) of N-propylnorapomorphine hydrochloride with 7.31 g. (0.07 mole) of cyclopropanecarbonyl chloride in 50 ml. of pyridine.

EXAMPLE 2

A solution of 20 ml. of acetic anhydride in 50 ml. of absolute pyridine was flushed with nitrogen and then treated all at once with 2.3 g. (0.0069 mole) of N-propylnorapomorphine hydrochloride. The mixture was stirred for about forty-eight hours, then filtered, concentrated in vacuo and reconcentrated twice again with benzene/hexane. The residue was taken into chloroform, washed once with dilute ammonium hydroxide, once with water, once with brine and then dried over anhydrous sodium sulfate. The solution was filtered and concentrated to dryness to give an oil that crystallized on trituration with ether. There was thus obtained 1.9 g. of crude product which was recrystallized from hexane to give two crops totaling 1.6 g. of N-propylnorapomorphine diacetate, m.p. 136.5°–137.5° C.

EXAMPLE 2A

Following a procedure similar to that described in Example 2 above N-propylnorapomorphine dipentanoate hydrochloride, m.p. 181°–183° C. (10.5 g. from ether), was prepared by reaction of 22.3 g. (0.12 mole) of pentanoic anhydride (i.e., valeric anhydride) with 9.96 g. (0.03 mole) of N-propylnorapomorphine hydrochloride in 50 ml. of pyridine.

EXAMPLES 3A–3D

It is contemplated that following a procedure similar to that described in Example 1, the following compounds of formula I can be prepared:

3A. N-Propylnorapomorphine bis-4-fluorobenzoate, by reaction of N-propylnorapomorphine with at least two molar equivalents of 4-fluorobenzoyl chloride in pyridine; and 3B. N-Propylnorapomorphine bis-4-bromobenzoate by reaction of N-propylnorapomorphine with at least two molar equivalents of 4-bromobenzoyl chloride in pyridine.

BIOLOGICAL TEST RESULTS

Results of tests in the caudate lesioned mouse test described above which were obtained on the compounds of the invention are given in the table below identified, in each case, by the example numbers above where their preparations are described. Corresponding data for reference apomorphine diesters described in German patent application No. 2,154,162 are given in a side-by-side relationship for a number of the species. The reference compounds, designated Ref. 1, Ref. 1B, Ref. 1C, Ref. 1D, Ref. 1E, Ref. 1F, Ref. 2 and Ref. 2A correspond, respectively, to the compounds of the invention identified by Examples 1, 1B, 1C, 1D, 1E, 1F, 2 and 2A and differ from the latter only in having a methyl group on the apomorphine nitrogen from instead of an n-propyl group as present in the instant compounds.

For purposes of comparison, the corresponding free phenolic compound, N-propylnorapomorphine disclosed by Archer U.S. Pat. No. 3,717,643 was similarly tested in the caudate lesioned mouse test, and the $ED_{50}$, on oral administration, was found to be 0.0032 m. mole/kg.

| Ex./Ref. | R | Dose/Kg. m. mole | Post-Drug Obs. Time (Hours) No. Mice Affected/No. Mice Tested | | | | | | | Molar $ED_{50}$ | Potency Ratio Claimed/Ref. Ester |
|---|---|---|---|---|---|---|---|---|---|---|---|
| | | | 1/2 | 1 | 2 | 4 | 6 | 24 | Total | | |
| Ex. 2 (Base) | $CH_3CO$ | 0.026 | 2/2 | 2/2 | — | 1/2 | 2/2 | 1/2 | 2/2 | | ≧16 |
| | | 0.052 | 1/4 | 1/4 | — | 1/4 | 3/4 | 0/4 | 3/4 | | |
| | | 0.104 | 2/4 | 3/4 | — | 1/4 | 2/4 | 2/4 | 3/4 | | |
| Ref. 2 (Base) | $CH_3CO$ | 0.208 | 0/4 | 0/4 | — | 0/4 | 0/4 | 1/4 | 1/4 | | — |
| | | 0.416 | 1/4 | 2/4 | — | 3/4 | 3/4 | 1/4 | 3/4 | | |
| Ex. 1 (Base) | $C_2H_5CO$ | 0.0052 | 0/4 | 0/4 | 0/4 | 0/4 | 0/4 | 0/4 | 0/4 | 0.01 | 10 |
| | | 0.013 | 3/4 | 3/4 | 3/4 | 3/4 | 2/4 | 0/4 | 3/4 | | |
| | | 0.026 | 4/4 | 4/4 | 3/4 | 3/4 | 1/4 | 0/4 | 4/4 | | |
| Ex. 1 | $C_2H_5CO$ | 0.0065 | 1/4 | 1/4 | 0/4 | 0/4 | 0/4 | NT | 1/4 | 0.0094 | 10 |

-continued

| Ex./Ref. | R | Dose/Kg. m. mole | Post-Drug Obs. Time (Hours) No. Mice Affected/No. Mice Tested | | | | | | | Molar $ED_{50}$ | Potency Ratio Claimed/Ref. Ester |
|---|---|---|---|---|---|---|---|---|---|---|---|
| | | | 1/2 | 1 | 2 | 4 | 6 | 24 | Total | | |
| (HCl) | | 0.13 | 3/4 | 2/4 | 0/4 | 0/4 | 0/4 | NT | 3/4 | | |
| | | 0.26 | 4/4 | 4/4 | 4/4 | 4/4 | 4/4 | NT | 4/4 | | |
| Ref. 1 (HCl) | $C_2H_5CO$ | 0.026 | 0/4 | 0/4 | 0/4 | 0/4 | 0/4 | 0/4 | 0/4 | 0.098 | — |
| | | 0.052 | 1/4 | 1/4 | 0/4 | 0/4 | 0/4 | NT | 1/4 | | |
| | | 0.104 | 5/12 | 5/12 | 0/12 | 0/12 | 0/12 | NT | 5/12 | | |
| | | 0.208 | 4/4 | 4/4 | 4/4 | 2/4 | 0/4 | 0/4 | 4/4 | | |
| Ex. 1A (Base) | $CH_3(CH_2)_2CO$ | 0.026 | 0/4 | 0/4 | 0/4 | 0/4 | 0/4 | 0/4 | 0/4 | | $\geq 8$ |
| | | 0.132 | 2/4 | 4/4 | 4/4 | 4/4 | 4/4 | 0/4 | 4/4 | | |
| Ex. 1B (Base) | $(CH_3)_2CHCO$ | 0.026 | 0/4 | 1/4 | — | 2/4 | 2/4 | 0/4 | 2/4 | | |
| | | 0.052 | 1/3 | 1/3 | — | 1/3 | 0/3 | 0/3 | 1/3 | | |
| Ref. 1B (Base) | $(CH_3)_2CHCO$ | 0.208 | 0/4 | 0/4 | — | 1/4 | 0/4 | 0/4 | 1/4 | | — |
| Ex. 2A (HCl) | $CH_3(CH_2)_3CO$ | 0.026 | 0/4 | 0/4 | 0/4 | 0/4 | 0/4 | 0/4 | 0/4 | | $\geq 3$ |
| | | 0.132 | 2/4 | 3/4 | 3/4 | 3/4 | 3/4 | 3/4 | 3/4 | | |
| Ref. 2A (HCl) | $CH_3(CH_2)_3CO$ | 0.208 | 0/4 | 0/4 | — | 0/4 | 0/4 | 0/4 | 0/4 | | — |
| | | 0.416 | 1/3 | 0/3 | — | 0/3 | 0/3 | 0/3 | 1/3 | | |
| Ex. 1C (Base) | $(CH_3)_3CCO$ | 0.026 | 0/2 | 0/2 | — | 2/2 | 2/2 | 0/2 | 2/2 | | $\geq 16$ |
| Ref. 1C (Base) | $(CH_3)_3CCO$ | 0.208 | 0/4 | 0/4 | — | 0/4 | 0/4 | 0/4 | 0/4 | | |
| | | 0.416 | 0/3 | 1/3 | — | 2/3 | 2/3 | 0/3 | 2/3 | | |
| Ex. 1D (Base) | $CH_3(CH_2)_{14}CO$ | 0.052 | 0/4 | 0/4 | — | 1/4 | 1/4 | 0/4 | 1/4 | | $\geq 8$ |
| | | 0.132 | 0/3 | 0/3 | — | 3/3 | 0/3 | 1/3 | 3/3 | | |
| Ref. 1D (Base) | $CH_3(CH_2)_{14}CO$ | 0.208 | 0/4 | 0/4 | — | 0/4 | 0/4 | 0/4 | 0/4 | | — |
| | | 0.416 | 0/4 | 0/4 | — | 0/4 | 0/4 | 0/4 | 0/4 | | |
| Ex. 1E (HCl) | $C_6H_5CO$ | 0.052 | 0/3 | 0/3 | — | 2/3 | 1/3 | 0/3 | 2/3 | | $\geq 8$ |
| Ref. 1E (Base) | $C_6H_5CO$ | 0.416 | 0/4 | 0/4 | — | 0/4 | 0/4 | 0/4 | 0/4 | | — |
| Ex. 1F (Base) | $4\text{-}ClC_6H_4CO$ | 0.132 | 0/4 | 1/4 | — | 0/4 | 1/4 | 0/4 | 1/4 | | $\geq 3$ |
| | | 0.208 | 1/3 | 0/3 | — | 2/3 | 3/3 | 1/3 | 3/3 | | |
| Ref. 1F (Base) | $4\text{-}ClC_6H_4CO$ | 0.416 | 0/4 | 0/4 | — | 0/4 | 0/4 | 0/4 | 0/4 | | — |
| Ex. 1G (Base) | $2\text{-}CH_3C_6H_4CO$ | 0.026 | 1/4 | 2/4 | 2/4 | 2/4 | 2/4 | 0/4 | 2/4 | 0.026 | |
| Ex. 1H (Base) | $4\text{-}CH_3C_6H_4CO$ | 0.026 | 0/4 | 0/4 | 0/4 | 0/4 | 0/4 | 0/4 | 0/4 | 0.07 | |
| | | 0.094 | 4/4 | 3/4 | 3/4 | 3/4 | 3/4 | 3/4 | 4/4 | | |
| Ex. 1J (Base) | $4\text{-}CH_3OC_6H_4CO$ | 0.0065 | 0/4 | 0/4 | 0/4 | 0/4 | 0/4 | 0/4 | 0/4 | 0.013 | |
| | | 0.026 | 2/4 | 4/4 | 3/4 | 2/4 | 2/4 | 0/4 | 4/4 | | |
| Ex. 1K (Base) | $3,5\text{-}(CH_3O)_2C_6H_3CO$ | 0.0016 | 0/4 | 0/4 | 0/4 | 0/4 | 0/4 | 0/4 | 0/4 | | |
| | | 0.0032 | 0/4 | 1/4 | 2/4 | 2/4 | 0/4 | 0/4 | 2/4 | | |
| | | 0.006 | 0/4 | 0/4 | 3/4 | 3/4 | 2/4 | 0/4 | 3/4 | | |
| | | 0.026 | 2/4 | 4/4 | 2/4 | 2/4 | 2/4 | 0/4 | 4/4 | | |
| Ex. 1L (HCl) | $3,4,5\text{-}(CH_3O)_3C_6H_2CO$ | 0.0052 | 0/4 | 0/4 | 0/4 | 0/4 | 0/4 | 0/4 | 0/4 | 0.015 | |
| | | 0.026 | 3/4 | 3/4 | 4/4 | 4/4 | 4/4 | 0/4 | 4/4 | | |
| Ex. 1M (Base) | $C_3H_5CO$ | 0.013 | 2/4 | 2/4 | 2/4 | 1/4 | 0/4 | 0/4 | 2/4 | 0.013 | |
| | | 0.026 | 4/4 | 3/4 | 3/4 | 3/4 | 3/4 | 0/4 | 4/4 | | |
| | | 0.132 | 4/4 | 4/4 | 4/4 | 4/4 | 4/4 | 0/4 | 4/4 | | |

We claim:

1. A member of the group consisting of (A) compounds having the formula:

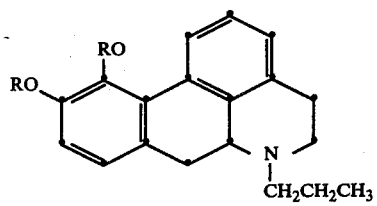

where R is alkanoyl having from two to 20 carbon atoms; benzoyl or benzoyl substituted by from one to three halogen atoms or by from one to three methyl or methoxy groups; or cyclopropanecarbonyl and (B) pharmaceutically acceptable acid-addition salts thereof.

2. A compound according to claim 1 where R is alkanoyl.

3. A compound according to claim 1 where R is benzoyl or benzoyl substituted by from one to three halogen atoms or by from one to three methyl or methoxy groups.

4. A compound according to claim 1 where R is cyclopropanecarbonyl.

5. N-Propylnorapomorphine diacetate according to claim 2.

6. N-Propylnorapomorphine dipropionate hydrochloride according to claim 2.

7. N-Propylnorapomorphine dibutanoate according to claim 2.

8. N-Propylnorapomorphine di-isobutyrate according to claim 2.

9. N-Propylnorapomorphine dipentanoate hydrochloride according to claim 2.

10. N-Propylnorapomorphine dipivaloate according to claim 2.

11. N-Propylnorapomorphine dihexadecanoate according to claim 2.

12. N-Propylnorapomorphine dibenzoate hydrochloride according to claim 3.

13. N-Propylnorapomorphine bis-4-chlorobenzoate according to claim 3.

14. N-Propylnorapomorphine bis-2-methylbenzoate according to claim 3.

15. N-Propylnorapomorphine bis-4-methylbenzoate according to claim 3.

16. N-Propylnorapomorphine bis-4-methoxybenzoate according to claim 3.

17. N-Propylnorapomorphine bis-3,5-dimethoxybenzoate hydrochloride according to claim 3.

18. N-Propylnorapomorphine bis-3,4,5-trimethoxybenzoate hydrochloride according to claim 3.

19. N-Propylnorapomorphine bis-cyclopropanecarboxylate according to claim 4.

* * * * *

UNITED STATES PATENT AND TRADEMARK OFFICE
CERTIFICATE OF CORRECTION

PATENT NO. : 4,126,616

DATED : November 21, 1978

INVENTOR(S) : William Banks Hinshaw and Jack Pearl

It is certified that error appears in the above-identified patent and that said Letters Patent are hereby corrected as shown below:

On the cover page, Column 1, "Assignee: William B. Hinshaw, New York, N.Y." should read --Assignee: Sterling Drug Inc., New York, N.Y.--.

Column 7, line 54, reads "two to 20 carbon atoms;" and should read --two to twenty carbon atoms;--.

Signed and Sealed this

Third Day of July 1979

[SEAL]

Attest:

LUTRELLE F. PARKER

*Attesting Officer*  *Acting Commissioner of Patents and Trademarks*